(12) United States Patent
Nakajima et al.

(10) Patent No.: US 9,872,550 B2
(45) Date of Patent: Jan. 23, 2018

(54) APPLICATOR

(71) Applicant: MITSUBISHI PENCIL COMPANY, LIMITED, Tokyo (JP)

(72) Inventors: Nobuyuki Nakajima, Gunma (JP); Shigeki Ooba, Gunma (JP); Tomoko Hasegawa, Gunma (JP); Yuuya Nagasaka, Gunma (JP); Keiichiro Takachiyo, Gunma (JP)

(73) Assignee: Mitsubishi Pencil Company, Limited, Tokyo (JP)

( * ) Notice: Subject to any disclaimer, the term of this patent is extended or adjusted under 35 U.S.C. 154(b) by 0 days.

(21) Appl. No.: 14/862,794

(22) Filed: Sep. 23, 2015

(65) Prior Publication Data

US 2016/0095415 A1    Apr. 7, 2016

(30) Foreign Application Priority Data

Oct. 1, 2014 (JP) .................. 2014-203210

(51) Int. Cl.
  *A45D 34/04* (2006.01)
  *A45D 40/28* (2006.01)
  *A61F 13/40* (2006.01)
  *A46B 11/00* (2006.01)
  *A46B 9/00* (2006.01)

(52) U.S. Cl.
  CPC ........... *A45D 34/04* (2013.01); *A45D 34/042* (2013.01); *A45D 40/28* (2013.01); *A46B 9/005* (2013.01); *A46B 11/0006* (2013.01); *A46B 11/0055* (2013.01); *A61M 35/006* (2013.01); *A46B 2200/1046* (2013.01)

(58) Field of Classification Search
  CPC .............................................. A45D 2200/1018
  USPC .................................. 401/261–266, 183–186
  See application file for complete search history.

(56) References Cited

U.S. PATENT DOCUMENTS

| 8,764,335 | B2 | 7/2014 | Uehara | |
|---|---|---|---|---|
| 8,777,506 | B2 | 7/2014 | Akaishi et al. | |
| 2003/0123917 | A1* | 7/2003 | Willat | A42B 3/121 401/6 |
| 2007/0186951 | A1* | 8/2007 | Gueret | A45D 34/00 132/320 |
| 2009/0283033 | A1 | 11/2009 | Akaishi et al. | |
| 2011/0129288 | A1 | 6/2011 | Uehara | |

FOREIGN PATENT DOCUMENTS

| JP | 2007-130157 A | 5/2007 |
|---|---|---|
| JP | 2010-042046 A | 2/2010 |

* cited by examiner

*Primary Examiner* — David Walczak
*Assistant Examiner* — Joshua Wiljanen
(74) *Attorney, Agent, or Firm* — Renner, Otto, Boisselle & Sklar, LLP

(57) ABSTRACT

To provide an applicator with an application body that is nonabsorbent and can uniformly spread and apply an application liquid over the surface to be applied on without scraping the applied liquid during application. The application body includes a membranous part that is easily deformable in applying liquid, and a cavity part enclosed by the membranous part, and constructed such that when the applying surface of the membranous part comes into contact with the surface to be applied on, the contact surface of the membranous part fits closely following the surface to be applied on by the pressure of the membranous part acting onto the contact surface of the surface to be applied on.

13 Claims, 6 Drawing Sheets

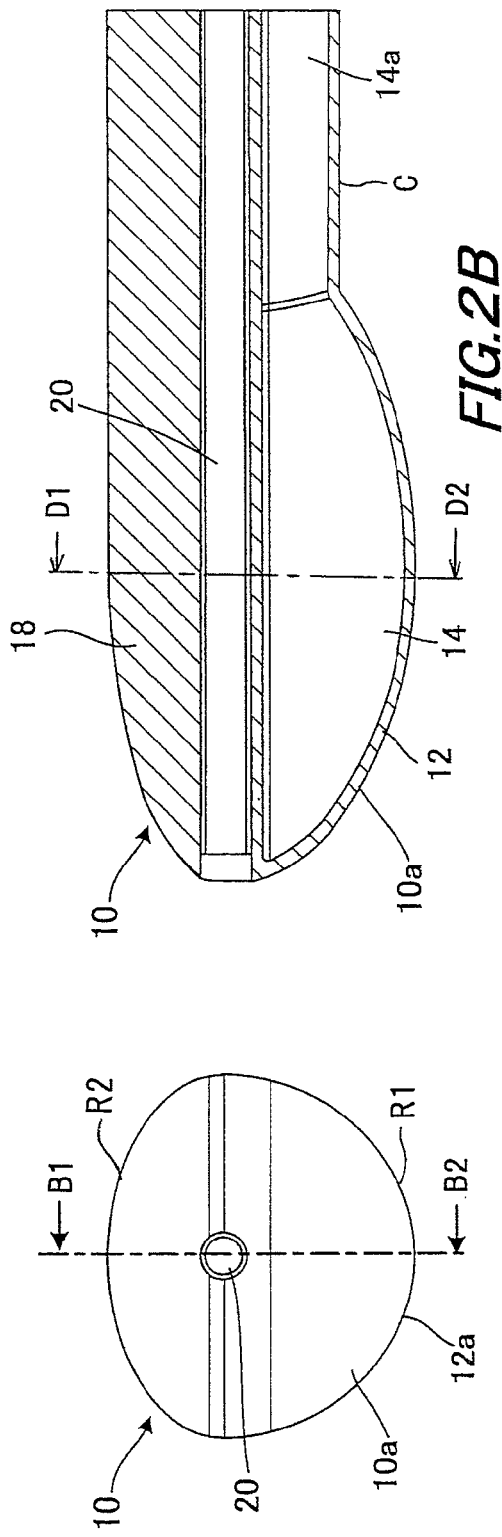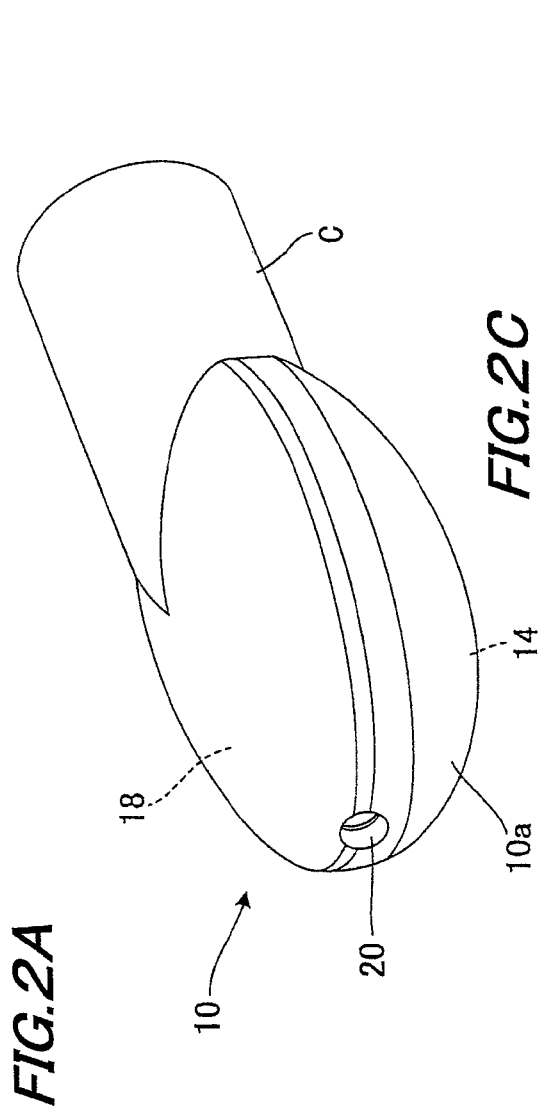

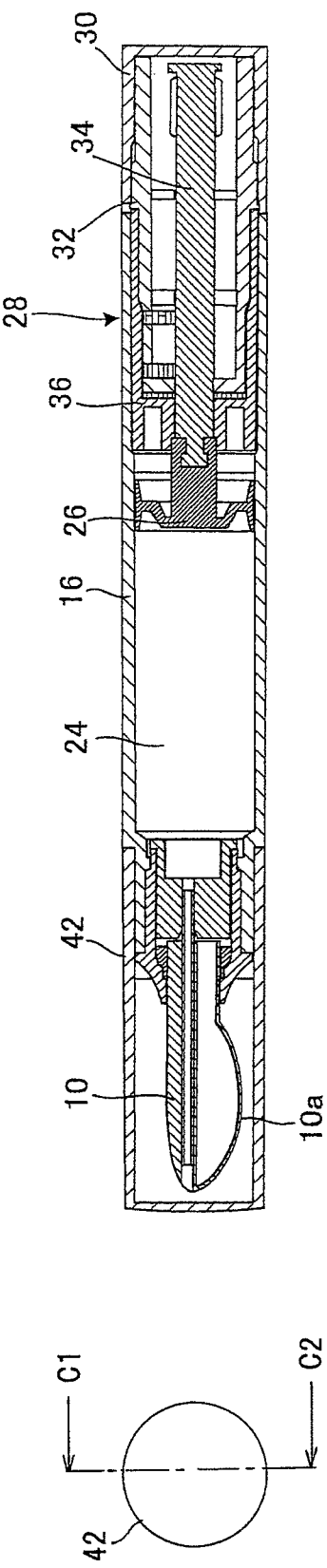
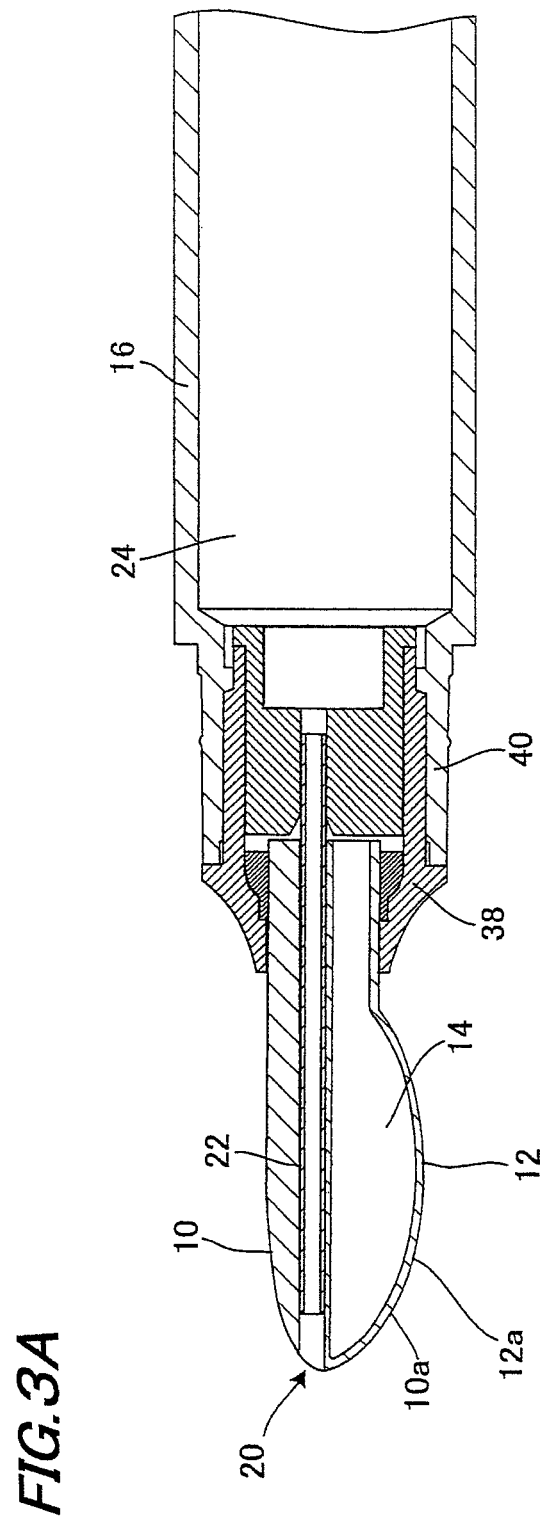

APPLICATOR

This Nonprovisional application claims priority under 35 U.S.C. §119 (a) on Patent Application No. 2014-203210 filed in Japan on 1 Oct. 2014, the entire contents of which are hereby incorporated by reference.

BACKGROUND OF THE INVENTION (1) Field of the Invention

The present invention relates to an applicator for cosmetics and medical use, which includes a container for applying a liquid and is required to uniformly apply a liquid of a relatively high viscosity and the like.

(2) Description of the Prior Art

Conventionally, there have been diverse proposals of applicators for applying liquid content solutions.

For example, there have been applicators that simply apply and spread a liquid with a cotton swab or sponge, and applicators that deliver a liquid and spread the liquid by its applying part of the container, disclosed in Japanese Patent Application Laid-open 2010-42046 (:Patent Document 1) and Japanese Patent Application Laid-open 2007-130157 (:Patent Document 2).

Usually, in liquid application the applicator is demanded to spread the liquid thinly and uniformly on the applied surface.

Though use of the fingers for application facilitates the liquid to spread uniformly, there is the problem that the fingers dirty.

Use of cotton swabs makes application work easy, but entails problems of uneven application and adhesion of fibers.

When sponge is used as the applying part, the liquid permeates over the sponge surface and is likely to produce spoils on the applied surface, causing hygienic problems. Further, there is also another problem that the component easy to permeate into sponge, such as a solvent of the liquid, is soaked into the sponge, changing the composition of the liquid retained in the applying part.

There have been also various kinds of applicators using brushes as their application body. A brush is an application body (applying part) formed of a bundle of fibers, hence it leaves fiber traces on the applied surface upon application, hence makes it difficult to apply the liquid thinly and uniformly.

In the applicator formed of silicone as proposed by Patent Document 1 of a liquid applicator, though the application body will not absorb the liquid the application body has approximately uniform elasticity because the application body is a silicone molding. Accordingly, when the application body having a substantially spherical surface is pressed against the applied surface, the pressure becomes higher at the center of the contact area on the sphere than in the surrounding of the center so that the liquid is not applied uniformly but is distributed thinner at the center the contact area and its vicinity than in the surrounding thereof. As a result, when the liquid is applied by moving the application body under this condition, the liquid after application will not become uniform but thin application of the liquid will appear along the trance of the center and its vicinity.

Further, when the applicator is of a flat application body, it is possible to apply uniform pressure if liquid application is performed on the surface of a perfect flat object. However, even in this case, if the application body is slightly inclined, or if the surface to be applied is not a perfect plane, the pressure becomes uneven so that the resultant thickness of the application liquid becomes uneven.

When a liquid delivery hole is formed in the application body as in Patent Document 1, the applied liquid is scraped by the edge forming and surrounding the hole as the applicator moves. As a result, the scraped trace is liable to appear on the liquid surface along the trace of the delivery hole.

In particular, a noticeable amount of liquid is scraped by the edge having the configuration shown in FIG. 6 of Patent Document 1.

When the applicator has an elastic spatula-like application body that can overall deform in conformity with the surface to be applied on as disclosed in Patent Document 2, the variation of the pressure of the application body across the width direction can be suppressed thanks to deformation of the application body following the applied portion. However, the pressing force from the applicator depending on elapsing time cannot be made uniform, so that the application thickness becomes uneven with respect to the direction of liquid application.

Further, this configuration also entails the problem that when a delivery hole is formed in the application body, the liquid is scraped by the edge forming and surrounding the hole so that no uniform application surface can be obtained.

RELATED ART DOCUMENTS

Patent Document 1

Japanese Patent Application Laid-open 2010-42046

Patent Document 2

Japanese Patent Application Laid-open 2007-130157

SUMMARY OF THE INVENTION

In view of the above circumstances, the present invention is to provide an applicator with an application body that is nonabsorbent and can uniformly spread and apply an application liquid over the surface to be applied on without scraping the applied liquid during application.

Now, the circumstances leading to the concept of the present invention will be described.

When a liquid is applied by the finger, the liquid can be easily and uniformly applied over the surface to be applied on even if the surface to be applied on is curved. The reasons can be considered as follows:

(a) There are soft sebum or oily protective substances and others inside the finger, and in application the sebum and others readily deform together with the outer surface (skin surface) and alters the shape, following the surface to be applied on, whereby the finger can apply uniform pressure on the surface to be applied on across the width of contact.

The soft sebum is not an elastic body, but can deform in conformity with the pressure.

(b) There are phalanx bone and nail on the rear side of the outer skin and sebum. In applying, the nail and bone will not bend or deform, hence the outer skin and sebum deform following the applied surface to be applied on.

(c) The nail width is narrower than the finger width, so that when liquid application is performed making use of the deformation of the skin and sebum, the nail will never come into contact with the applied surface even if the finger is inclined, hence will not scrape the applied liquid from the applied surface.

(d) The skin surface is nonabsorbent or will not absorb the liquid, hence the liquid composition will not change.

(e) When the application liquid is applied with the finger, the application liquid is directly delivered from the container to the finger or the surface to be applied on and then is spread by the finger. Accordingly, there is no way the edge around the delivery hole of the container scrapes the applied liquid.

The inventors hereof have prepared applicators having the above characteristics and functions and devised an applicator of the invention that can easily and uniformly apply an application liquid similarly to the fingers. The applicator of the invention is configured as follows:

(1) According to the present invention, an applicator for applying an application liquid on a surface to be applied on by means of an application body, the applicator comprising:

an application body comprising:

a membranous part that is easily deformable in applying liquid; and a cavity part enclosed by the membranous part, wherein when an applying surface of the membranous part comes into contact with a surface to be applied on, the applying surface of the membranous part in contact with the surface to be applied on follows to a contact surface of the surface to be applied on by a pressure of the membranous part acting onto the contact surface of the surface to be applied on.

As described with the related Patent Documents, in the liquid application with a usual applying part formed of one kind of soft elastic material such as silicone rubber, sponge or the like suggested as a usual soft applying part, it is inevitable that the pressure acting on the applied surface becomes higher at the most depressed portion of the applying part, so that the thickness of the applied liquid will not become uniform with respect to the width direction of the applying part.

Accordingly, the above problem can be solved by an applying part formed of a soft deformable outer skin with a cavity part (space) in which a filler that can deform at the time of application is stuffed.

The membranous part of the outer skin may be formed of rubber (silicone rubber, urethane rubber, isoprene rubber (IR), butadiene rubber (BR), styrene butadiene rubber (SBR), chloroprene rubber (CR), acrylonitrile butadiene rubber (NBR), butyl rubber (IIR), ethylene-propylene rubber (EPM), chlorosulfonated polyethylene rubber (CSM), acryl rubber (ACM), fluoro rubber (FKM), natural rubber, and others) so as to make it thin and hence can be easily deformed. For the rubber of the outer skin, it is necessary to select an easy-to-handle rubber hardness depending on the application liquid. The rubber hardness is preferably 20 to 60. Rubber with a rubber hardness of less than 20, is soft and easy to deform but liable to rapture. Rubber with a rubber hardness exceeding 60 cannot provide sufficient deformation so that it is difficult to make the applied liquid uniform in thickness. The rubber hardness is more preferably 20 to 40.

The interior of the cavity part preferably contains a filler that is not elastically deformed but is easy to deform and does not have big repulsion. The filler does not need to be fully charged so that the outer skin will be in a pressed state to have definite tension, but is preferably charged so that the outer skin will be more or less slacken like a finger.

(2) In the present invention, it is preferable that the cavity part contains a substance that forms a soft gel after filling by cross-linking reaction.

When a gelatinous material is stuffed as a filler into the cavity part (the interior of the outer skin), the pressure acting when the liquid is applied becomes approximately uniform. As a result, it is possible to apply the liquid with uniform thickness.

When, for example a two-component reaction liquid silicone or the like is used as the gelatinous material, the two liquids can be charged into the outer skin and then made to form a soft gel by cross-linking.

In this case, the liquid silicone and the like are charged into the cavity part to fit to the interior shape of the outer skin, then cross-linked to form a gel. Because of gel-like physical properties the filler will not easily flow out through the filler hole even though pressure is applied during application, so that it is not necessary to seal the filler hole. Hence, the production of the application body can be simplified.

The gel-like material preferably has a hardness (penetration) of 30 to 90.

(3) In the present invention, it is preferable that the cavity part contains a substance that foams after filling to form a soft sponge.

Stuffing soft spongy material into the outer skin also produce the advantage of the invention. In this case, a reaction type sponge substance such as foamed urethane is made to react inside the cavity part so as to completely fill the hollow without causing the filler to spill out from the filler hole when the applicator is used for application.

As to the suitable hardness of the sponge, the sponge preferably presents a repulsive force of 10N to 350 N when a test piece of the sponge of 390 mm long, 390 mm wide and 50 mm thick is compressed by 25%.

(4) In the present invention, it is preferable that the cavity part contains a filler that has been made viscous by a thickener.

When using a thickener to form a gel-like filler and fill the cavity part, the agent couples with the filler due to gravity to form a gel-like lump.

Use of various kinds of thickeners, either water-based or oil-based, facilitates production of gel-like fillers of different softness.

Since the thickener is selectable, use of a thickener for food or cosmetic purposes can secure safety even if the content liquid leaks out and comes in contact the user's body.

(5) In the present invention, it is preferable that the cavity part contains air, and the air is tightly sealed in the cavity part by adjusting the thickness of the membranous part, or a shape of the cavity part is maintained by virtue of an elastic force of the membranous part in a state such that an air is not sealed in the cavity part.

When air can be used as the filler of the cavity part (the interior of the outer skin of the membranous part), it is possible to cut down the cost.

In particular, it is not necessary to seal the air inside the cavity part if the thickness and the interior space of the outer skin are adjusted so as to be able to produce suitable pressure when the application body is pressed for application.

In this case, however, the application body needs to practically restore its original shape after use due to elasticity of the outer skin.

It goes without saying that there is no problem with use of a type in which the cavity part is sealed up so as not to permit air leakage.

Also, in this case, it is preferable that air is not fully charged so that the charged air will pressurize the outer skin, but is charged so as to create slacks more or less.

(6) In the present invention, it is preferable that a liquid delivery hole is arranged in an area other than the applying surface of the application body.

Provision of a liquid delivery hole in the area other than the applying surface makes it possible to eliminate application unevenness due to scraping of the liquid during application by the part surrounding the liquid delivery hole.

(7) In the present invention, it is preferable that the application body is formed with a rigid part that has a greater rigidity than the applying surface side and is arranged on an opposite side of the applying surface with respect to a liquid flow passage so as to prevent overall distortion of the application body during liquid application.

When the entire applying part is formed of an outer skin and a filler, it is difficult to easily and uniformly apply the liquid in a wide area because the application body is bent overall at the time of liquid application.

In contrast, when a finger is used in applying, the finger has a nail and bone, which support the applying part (i.e., the pad of the finger) formed of the skin and sebum, thereby enabling the finger to achieve easy liquid application.

In order to make the application body produce the same effect as the finger does, it is necessary to provide a rigid part on the opposite side of the applying part formed of the outer skin and the filler.

The structure for providing rigidity to the application body can be configured by thickening the opposite side of the soft elastic material (rubber) forming the outer skin of the applying part to impart rigidity, or by arranging a resin molding, metal part or the like on the opposite side of the applying part to impart rigidity as a whole.

Here, a through-hole for the liquid delivery hole maybe formed in an reinforcement portion for securing rigidity, and this rigidity allows the user to put the liquid at a desired position easily and reliably.

(8) In the present invention, it is preferable that the application body is formed so that the applying surface side is wider than the rigid part when viewed in a cross section perpendicular to the liquid flow passage.

To spread the liquid uniformly, it is important that the soft deformable applying surface alone comes into contact with a surface to be applied on. If application is performed while the portion (rigid portion) provided for making the application body rigid comes into contact, the applied liquid is scraped by the performance of spreading so that application of uniform thickness cannot be achieved.

In order to solve this problem, the applying surface needs to be formed so as to spread outside beyond the rigid portion when the liquid is applied.

Specifically, when the applying part is viewed from the top (from the side of the rigid portion), it is necessary that the soft applying part can be seen outside the rigid portion.

(9) In the present invention, it is preferable that the applying surface of the application body is formed of a nonabsorbent surface.

When the outer skin of the applying surface is nonabsorbent, the applying surface will not absorb the solvent component alone, which is liable to be absorbed, of the liquid to be applied, hence there is no risk that the liquid composition varies.

Advantages of the Invention

According to the applicator of the present invention, the application body is so formed that when the membranous applying surface comes into contact with the surface to be applied, the membranous contact surface is deformed following the surface to be applied on by the pressure acting on the contact surface. As a result, this application body can produce excellent advantage in applying the liquid by pressing the application body against the surface to be applied on, that is, it is possible to apply the liquid smoothly with a uniform thickness even if the surface to be applied on is curved.

BRIEF DESCRIPTION OF THE DRAWINGS

FIG. 2A is a front view showing an application body provided for an applicator according to a second embodiment of the present invention, viewed from a delivery port side;

FIG. 2B is a vertical cross-sectional view taken along plane B1-B2 of FIG. 2A;

FIG. 2C is a perspective view showing the application body according to the second embodiment;

FIG. 3A is a front view showing an applicator according to the second embodiment, viewed from a cap 2 side;

FIG. 3B is a vertical cross-sectional view of the entire applicator, taken along plane C1-C2 of FIG. 3A;

FIG. 3C is an enlarged cross-sectional view showing the application body and its surroundings of FIG. 3B;

DESCRIPTION OF THE PREFERRED EMBODIMENTS

Figure 1A:
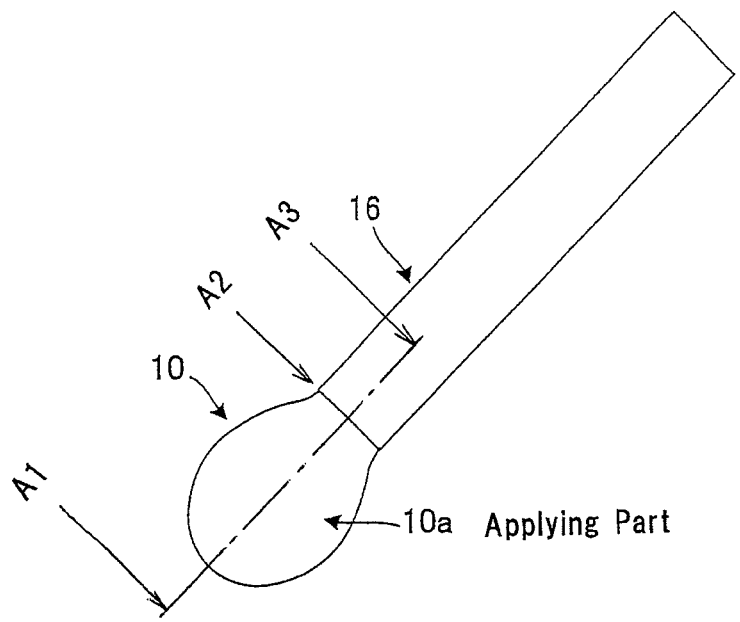
FIG. 1A is a side view of an applicator according to a first embodiment of the present invention.
Figure 1B:
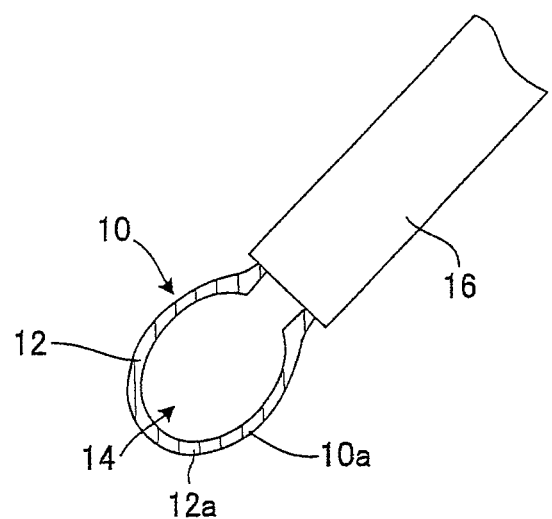
FIG. 1B is a side view of the applicator including a vertical cross-sectional view taken along plane A1-A2 of FIG. 1A.
Figure 1C:
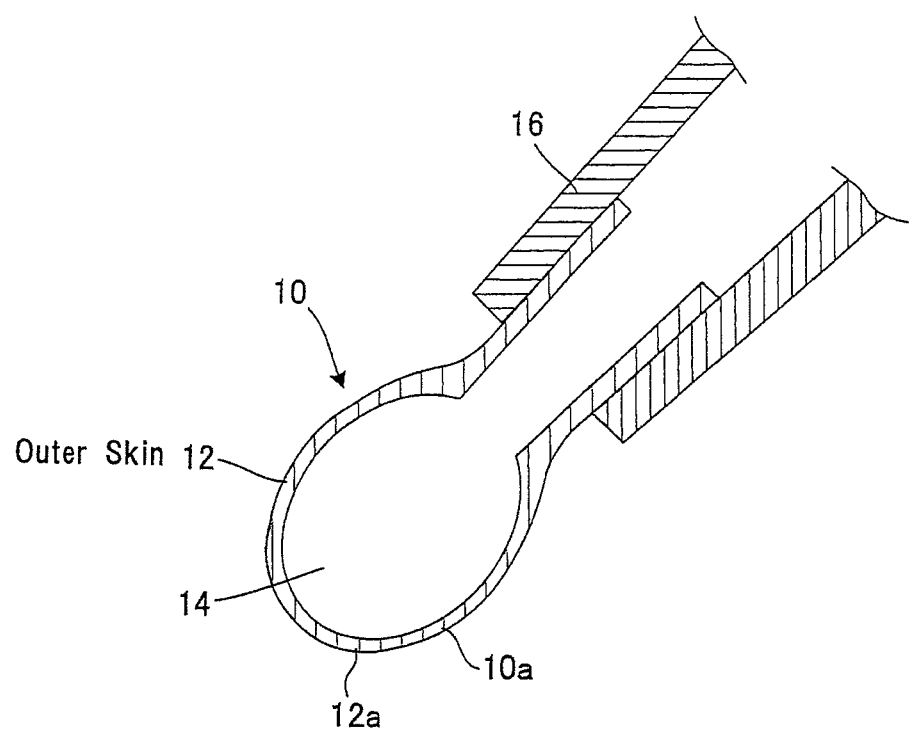
FIG. 1C is an enlarged vertical cross-sectional view taken along plane A1-A3 of FIG. 1A.

Now, the embodiments of the present invention will be described in detail with reference to the accompanying drawings.

Hereinbelow, FIGS. 1A to 1C, FIGS. 2A to 2C, FIGS. 3A to 3C and FIGS. 4A to 4C may also be generally mentioned as FIG. 1, FIG. 2, FIG. 3 and FIG. 4, respectively.

FIG. 1 is an illustrative view of the applicator according to the first embodiment of the present invention.

The applicator according to the first embodiment is an applicator for applying an application liquid on a surface of an object to be applied on by means of an application body 10.

The application body 10 has a membranous part 12 that easily deforms at the time of application and a cavity part 14 enclosed by the membranous part.

The application body 10 is configured so that when an applying surface 12a of the membranous part 12 comes into contact with the surface to be applied on, a contact surface of the membranous part 12 fits closely following a contact area of the surface to be applied on by virtue of the pressure of the membranous part 12 onto the contact area of the applied surface.

Specifically, as shown in FIG. 1 the application body 10 is formed of the membranous part 12 as an outer skin and the cavity part 14 alone and is a flexible bag-like molding having an approximately spherical front part and a cylindrical rear part. The application body 10 has such a simple configuration that the front part plays a role of an applying part 10a, which is supplied with a liquid and brought into contact with the surface to be applied on, thereby being able to perform application. The cylindrical rear part of the application body 10 is fixed to a front end of a cylindrical barrel 16.

The membranous part 12 of the application body 10 is formed of rubber (e.g., silicone rubber) while the cavity part 14 of the application body 10 is filled with an easily deformable soft substance such as a gel (liquid silicone), sponge or the like, or air, to form soft applying part 10a.

The applicator according to the second embodiment will be described.

FIG. 2 is the illustrative view of the application body used for the applicator according to the second embodiment. FIG. 3 is the illustrative view of the entire applicator. FIG. 4 is the illustrative view showing use states of the applicator.

As shown in FIG. 2, an application body 10 according to the second embodiment has: a membranous part 12 forming an applying surface 12a; a rigid reinforcement part 18 formed thicker than the applying surface 12a; and a liquid delivery hole 20 formed between the former two parts. The rigid reinforcement part 18 is formed on the opposite side of the applying surface 12a of the membranous part 12 with respect to the liquid delivery hole 20. The reinforcement part 18 is provided so that the application body 10 as a whole will not deform when the applicator is used for application.

The application body 10 is molded of a liquid silicone (either LIM type or millable type can be used). FIG. 2 shows the configuration of the outer skin of the membranous part 12.

The application body 10 can be molded in a millable type so that the membranous part 12 of silicone rubber has a thickness of 0.4 mm and a rubber hardness of 20, 30 or 40. As to usability, the softer the rubber is, the more flexible and confortable feeling can be obtained when the applicator is used.

As shown in FIG. 2, in the application body 10, the thin membranous part 12 forms an applying part 10a, inside which a hollow or cavity part 14 is formed. As shown in FIG. 2A, the curved surface on the bottom side view from the front side has a radius of curvature R1, which is smaller than the radius of curvature R2 of the curved surface on the top side viewed from the front side. So the curved surface on the bottom side swells more to simulate a human finger. The bottom side part having the radius of curvature R1 is the applying part 10a of the membranous part 12 having the cavity part 14. Formed on the other side of the applying part 10a (the curved surface having the radius of curvature R2) is the thick reinforcement part 18, the rubber thickness of the reinforcement part 18 being greater than that of the membranous part 12. The applying part 10 is totally formed of soft rubber, but the reinforcement part 18 is thicker than the applying part 10a, so that the top side forming the reinforcement part 18 produces rigidity.

Here, as shown in FIG. 2, the application body 10 is shaped so that the applying part 10a is formed thicker in diameter than the cylindrical part, designated at C, to be coupled with the barrel 16 (FIGS. 3B and 3C) located in the rear of the application body, thus the applying part 10a is formed into a wide area for easy application. The liquid delivery hole (liquid flow passage) 20 is penetrated through between the applying part 10a and the reinforcement part 18. Since the opening of the liquid delivery hole 20 is away from the applying part 10a, this arrangement is advantageous, or makes it possible to prevent the part forming and surrounding the liquid delivery hole from scraping the applied liquid during liquid application.

In order to provide a more stable rigidity, it is possible to insert a resin molding or a metal part (metal pipe, stainless pipe) into the reinforcement part 18 (rigid part) of rubber.

FIGS. 3B and 3C show a configuration of an applicator in which a stainless pipe 22 is inserted as a reinforcing member in the application body 10, particularly in the liquid delivery hole 20.

Alternatively, it is possible to attach the applying part 10a to a reinforcing member. That is, in order to secure the necessary rigidity, a rubber molding to form an applying part 10a of a membranous part and a cavity part may be attached to a resin molding or metal part (mainly forming a reinforcement part) to construct an application body with rigidity.

Similarly to the first embodiment, charging an easily deformable substance into the cavity part 14 inside the outer skin makes it possible to perform liquid application free from unevenness without causing the outer skin to generate uneven pressure during the applied liquid is spread.

FIGS. 3B and 3C show the applicator in which a hard pipe 22 of stainless steel or the like is inserted in the liquid delivery hole 20 in order to make the entire application body 10 more rigid.

Arranged inside the barrel 16 is a reservoir (container) 24 for storing a liquid, a piston 26 and an advancing mechanism 28 that advances the piston 26 to feed the liquid from the reservoir 24 to the application body 10. The piston 26 is a structure that has a soft outer peripheral part put and slid in liquid-tight contact with the inner wall of the reservoir 24 to forward the liquid to the application body 10.

The advancing mechanism 28 includes a control handle 30 at the rear end of the barrel 16 and an advance cylinder 32 that is fixed with respect to the rotational direction of the handle 30 and arranged inside the barrel 16. Arranged in the advance cylinder 32 a threaded rod 34 for advancing the piston 26 so that the rod 34 is restrained from rotating and can freely move in the advancing and retracting directions. The threaded rod 34 is formed with a variant outer shape and male-threaded. Fixed inside the barrel 16 is a thread body 36. The thread body 36 is configured to mesh a female thread formed inside the thread body 36, with the threaded rod 34. The piston 26 is rotatably fitted at the front end of the threaded rod 34, so that the piston 26 propels the liquid in the reservoir 24 toward the application body 10 as the threaded rod 34 advances.

The cylindrical part C in the rear part of the application body 10 is fitted into a front barrel 38 (FIG. 3C) that is inserted and fixed to a joint 40 at the front end of the barrel 16.

The applicator shown in FIG. 3 is formed with the liquid delivery hole 20 that is connected to the reservoir (container) 24. This liquid delivery hole 20 is arranged at the tip of the applying part 10a, in the area other than the applying surface 12a. A necessary amount of liquid is discharged and placed over the surface to be applied on from the liquid delivery hole 20 by means of the advancing mechanism 28, then the liquid is spread by rubbing the liquid with the applying part 10a. Here, the applicator shown in FIG. 3 is constructed such that a cap 42 is removably fitted to the front end of the barrel 16 when the applicator is unused. When the application body 10 is unused, the application body 10 is covered by the cap 42 so as to prevent drying out of the liquid delivery hole 20 and the applying surface 12a of the application body 10, thus securing smooth application of the application liquid when the applicator is used next time.

In the present embodiment, the liquid delivery hole 20 is not formed in the applying surface 12a. Therefore, there is no risk that the liquid delivered from the liquid delivery hole 20 is scraped at once by the structure forming the liquid delivery hole 20. Accordingly, the liquid can be applied with a uniform thickness and/or uniform width.

In the application body 10, the cavity part 14 is open to the rear (opening 14a), as shown in FIG. 2. That is, since the core is pulled out when the application body 10 is molded, the opening 14a is unavoidably formed. However, use of a gelatinous material that reacts and cross-links with liquid silicone or the like, as the filler to be filled into the cavity part 14, makes it possible to prevent the filler from being pushed out from the opening 14a on the rear side.

Similarly, when sponge such as foaming urethane or the like is charged into the cavity part 14 of the outer skin (applying surface 12a) and then foamed, the sponge will not be pushed out from the opening 14a when the applicator is used.

Alternatively, when a gelatinous material is prepared using a thickener such as guar gum or the like and charged into the cavity part 14, the material is molded so as to become fitted to the interior shape with time after filling, so that the material will not be pushed out from the opening 14a.

The ease of the filler to be pushed out from the opening 14a when the applicator is used differs depending on the viscosity. When a gelatinous thickener is used, there is a risk that the base liquid (solvent) evaporates and the volume of the gel may decrease. In this case, the mouth (opening 14a) needs to be sealed.

On the other hand, if the cavity part 14 is not filled with any soft material, or if the applying part 10a that is not filled with any filler is used as is, this configuration is cost effective. In this case, the elasticity can be adjusted by the thickness of the membranous part 12 and selection of rubber material.

Use of the applying part 10a with its cavity left as is, can be realized by sealing off the opening 14a of the cavity part 14 inside the applying part 10a. The air therein does not need to be pressurized. Even though the applying part is, more or less, flabby, there occurs no problem as long as the applying part has 'tension' when used.

Alternatively, the outer skin's rubber thickness (the thickness of the membranous part 12) may be made greater so as to slightly increase rigidity, whereby it is possible to provide a usable configuration even if the opening 14a of the cavity part 14 inside the membranous part 12 (outer skin) is connected to the atmosphere.

Next, description will be made on the conditions of the application body during use.

Figure 4A:
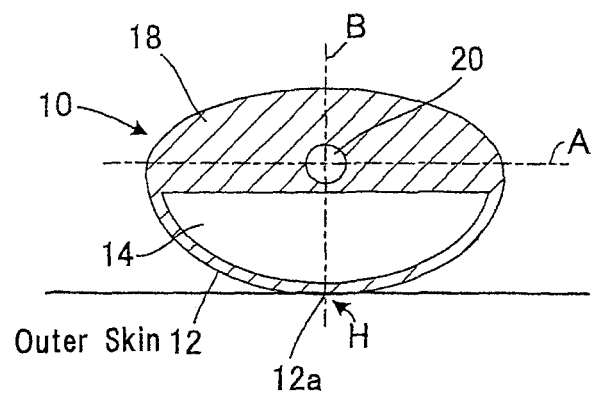
FIG. 4A is an illustrative view showing a use state of the applicator, based on the vertical cross-sectional view of the application body taken along plane D1-D2 of FIG. 2B.
Figure 4B:
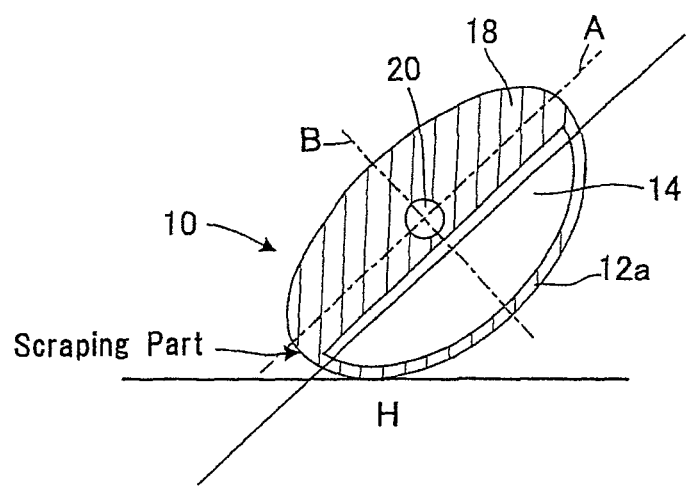
FIG. 4B is an illustrative view showing a use state when the application body of FIG. 4A is inclined; and, FIG. 4C is a vertical sectional view of a variational example of the applicator body shown in FIGS. 4A and 4B.

When the applying part 10a during application is viewed in section as shown in FIG. 4A, there are two parts, the part of the applying surface 12a (applying part 10a) of the application body 10 and the thick ridge part (reinforcement part 18). The cross section of each area will be considered. The applied surface of the applied object is denoted by H (FIGS. 4A and 4B). An additional line A (FIGS. 4A and 4B) is drawn in the width direction of the application body 10 so as to pass through the liquid delivery hole (liquid flow passage) 20, whereas another additional line B (FIGS. 4A and 4B) is drawn in the thickness direction.

In the application body 10, in a case where the cross section of the applying part 10a inclusive of the cavity part 14 is approximately the same as the cross section of the reinforcement part 18, when the application body 10 is placed with the applying surface 12a inclined relative to the surface H of the object to be applied on, the corner of the reinforcement part 18 comes into contact immediately with the area where the liquid is being spread on the applied surface because the cross sections of the applying part 10a and the reinforcement part 18 are equal to each other as shown in FIG. 4B. As a result, the rigid corner may scrape the liquid off the applied surface, giving rise to the risk of making liquid application uneven in thickness and lack of uniformity in width.

Figure 4C:
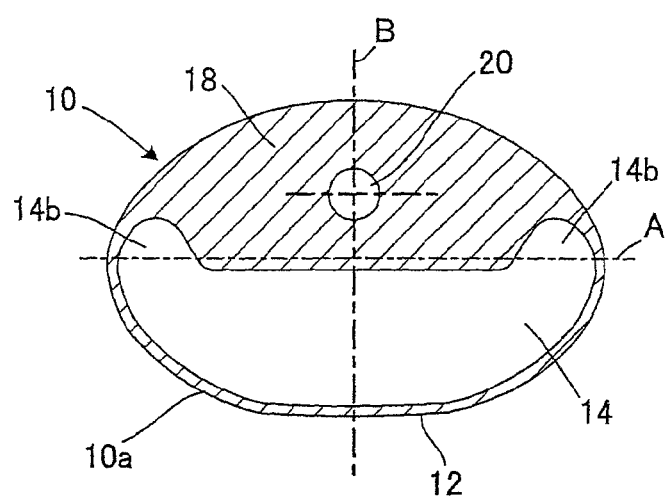

To deal with this situation, a variation of the application body 10 is shown in FIG. 4C. An application body 10 in FIG. 4C has a configuration in which the cavity part 14 inside the outer skin is extended toward (spread out into) the reinforcement part, forming extended cavity portions 14b. With this arrangement, the extended cavity portions 14b are hollowed so that the width of the applying part 10a having extended cavity portions 14b is greater than the width of the solid rigid part 18, with respect to the width direction A. That is, the extended cavity portions 14b being softer and elastically more deformable than the corner of rigid part 18 are formed outside the rigid part with respect to the width direction A. Accordingly, the corner of the rigid part (reinforcement part) 18 do not come close to, or into contact with, the applied surface H of the applied object even if the liquid is applied with the application body 10 inclined. Thus, the applied liquid will not, or is unlikely to, be scraped.

It is noted that the present invention should not be limited to the above embodiments, but various changes and modifications can be made within the scope of the invention. For example, a pipe may be inserted as a reinforcing member into the application body. Or two-color molding may be used to form a reinforcement part. Further, different liquid advancing mechanisms other than that herein, such as click-type and others, may be used.

INDUSTRIAL APPLICABILITY

The applicator of the invention can be applied to applicators for applying various kinds of application liquids for makeup, medical use and others.

Description of Reference Numerals

10 application body
10a applying part
12 membranous part
12a applying surface
14 cavity part
16 barrel
18 reinforcement part (rigid part)
20 liquid delivery hole (liquid flow passage)
22 pipe
24 reservoir
28 advancing mechanism
H surface to be applied on.

What is claimed is:

1. An applicator for applying an application liquid on a surface to be applied on by means of an application body, the applicator comprising:
   an application body comprising:
      a membranous part that is easily deformable in applying liquid; and
      a cavity part enclosed by the membranous part, wherein when an applying surface of the membranous part comes into contact with a surface to be applied on, the applying surface of the membranous part in contact with the surface to be applied on follows to a contact surface of the surface to be applied on by a pressure of the membranous part acting onto the contact surface of the surface to be applied on, and a liquid delivery hole is arranged in an area other than the applying surface of the application body.

2. The liquid applicator according to claim 1, wherein the applying surface of the application body is formed of a nonabsorbent surface.

3. The liquid applicator according to claim 1, wherein the cavity part contains a substance that forms a soft gel after filling by cross-linking reaction.

4. The liquid applicator according to claim 1, wherein the cavity part contains a substance that foams after filling to form a soft sponge.

5. The liquid applicator according to claim 1, wherein the cavity part contains a filler that has been made viscous by a thickener.

6. The liquid applicator according to claim 1, wherein the cavity part contains air, and the air is tightly sealed in the cavity part by adjusting a thickness of the membranous part, or a shape of the cavity part is maintained by virtue of an elastic force of the membranous part in a state such that an air is not sealed in the cavity part.

7. An applicator for applying an application liquid on a surface to be applied on by means of an application body, the applicator comprising:

an application body comprising:
  a membranous part that is easily deformable in applying liquid; and
  a cavity part enclosed by the membranous part,
wherein
when an applying surface of the membranous part comes into contact with a surface to be applied on, the applying surface of the membranous part in contact with the surface to be applied on follows to a contact surface of the surface to be applied on by a pressure of the membranous part acting onto the contact surface of the surface to be applied on, and the application body is formed with a rigid part that has a greater rigidity than the applying surface side and is arranged on an opposite side of the applying surface with respect to a liquid flow passage so as to prevent overall distortion of the application body during liquid application.

8. The liquid applicator according to claim 7, wherein the application body is formed so that the applying surface side is wider than the rigid part when viewed in a cross section perpendicular to the liquid flow passage.

9. The liquid applicator according to claim 7, wherein the applying surface of the application body is formed of a nonabsorbent surface.

10. The liquid applicator according to claim 7, wherein the cavity part contains a substance that forms a soft gel after filling by cross-linking reaction.

11. The liquid applicator according to claim 7, wherein the cavity part contains a substance that foams after filling to form a soft sponge.

12. The liquid applicator according to claim 7, wherein the cavity part contains a filler that has been made viscous by a thickener.

13. The liquid applicator according to claim 7, wherein the cavity part contains air, and the air is tightly sealed in the cavity part by adjusting a thickness of the membranous part, or a shape of the cavity part is maintained by virtue of an elastic force of the membranous part in a state such that an air is not sealed in the cavity part.

\* \* \* \* \*